(12) United States Patent
Lee

(10) Patent No.: US 6,262,072 B1
(45) Date of Patent: Jul. 17, 2001

(54) ORALLY ADMINISTERED ANTIMICROBIAL PHARMACEUTICAL FORMULATIONS OF CIPROFLOXACIN

(75) Inventor: Fang-Yu Lee, Tachia (TW)

(73) Assignee: Yung Shin Pharmaceutical Industrial Co. Ltd., Taichung (TW)

( * ) Notice: Subject to any disclaimer, the term of this patent is extended or adjusted under 35 U.S.C. 154(b) by 0 days.

(21) Appl. No.: 09/415,067

(22) Filed: Oct. 12, 1999

(51) Int. Cl.$^7$ .......................... A61K 31/47; A61K 31/445
(52) U.S. Cl. ........................ 514/312; 514/315; 514/317
(58) Field of Search ................................. 514/312, 315, 514/317

(56) References Cited

U.S. PATENT DOCUMENTS

| | | | |
|---|---|---|---|
| 4,284,629 | 8/1981 | Grohe et al. | 424/246 |
| 4,499,091 | 2/1985 | Wentland et al. | 514/254 |
| 4,668,784 | 5/1987 | Mascellani et al. | 544/32 |
| 4,670,444 | 6/1987 | Grohe et al. | 514/300 |
| 5,286,754 | 2/1994 | Streuff et al. | 514/772.3 |

OTHER PUBLICATIONS

Yoshimi Shrai, et al, Biol. Pharm, Bull. 16(2):172–177 (1993).

Primary Examiner—Kevin E. Weddington
(74) Attorney, Agent, or Firm—Fei-Fei Chao; Venable, Baejier, Howard & Civiletti, LI

(57) ABSTRACT

The invention provides three orally administered ciprofloxacin formulations: The first formulation comprises 60–75 wt % of ciprofloxacin or at least one of pharmacologically acceptable salt; 0.3–10 wt % of pregelatinized starch as binder; 5–30 wt % of lactose as diluent; 1–10 wt % of sodium starch glycolate as disintegrant; and 0.5–2 wt % of magnesium stearate as lubricant. The second formulation comprises 60–75 wt % of ciprofloxacin or its pharmacologically acceptable salt; 1–5 wt % of polyvinyl pyrrolidone as binder; 5–30 wt % of lactose as diluent; 1–10 wt % of sodium starch glycolate as disintegrant; and 0.5–2 wt % of magnesium stearate as lubricant. The third formulation comprises 60–75 wt % of ciprofloxacin or at least one of pharmacologically acceptable salt; 1–8 wt % of polyvinyl alcohol as binder; 5–30 wt % of lactose as diluent; 1–10 wt % of sodium starch glycolate as disintegrant; and 0.5–2 wt % of magnesium stearate as lubricant. The ciprofloxacin or its pharmacologically acceptable salts, the binder, the diluent, the disintegrant, and the lubricant are first mixed in a dry state to form a powder mixture, followed by mixing with a water-solvent solution to convert the dry powder mixture into a wet powder mixture before grinding and granulating the wet powder mixture into wet granules, which are further dried to form dry granules. The above three formulations do not contain cellulose.

16 Claims, 6 Drawing Sheets

ORALLY ADMINISTERED ANTIMICROBIAL PHARMACEUTICAL FORMULATIONS OF CIPROFLOXACIN

FIELD OF THE INVENTION

This invention relates to orally administered antimicrobial formulations which contain, as an active ingredient, 1-cyclopropyl-6-fluoro-1,4-dihydro-4-oxo-7-(1-piperazinyl)-3-quinolinecarboxylic acid (also called ciprofloxacin) or its pharmacologically acceptable salts (preferably, HCl salt monohydrate) in a solid dosage form. The ciprofloxacin is combined with effective amounts of binders (preferably, pregelatinized starch, polyvinyl pyrrolidone, or polyvinyl alcohol), diluents (preferably, lactose), disintegrants (preferably, sodium starch glycolate), wetting agent (preferably, sodium lauryl sulfate), and lubricants (preferably, magnesium stearate) to form granules or tablets. This invention also relates to methods for making the ciprofloxacin-containing tablets or granules using dry-wet-dry granulation processing before compression to tablets with granulation performed in a wet state. The tablets or capsules made from these formulations possess superior biological availability and excellent storage stability.

BACKGROUND OF THE INVENTION 1-cyclopropyl-6-fluoro-1,4-dihydro-4-oxo-7-(1-piperazinyl)-3-quinoline carboxylic acid (also known as ciprofloxacin) belong to the class of quinolones, which are known to possess a broad antibacterial spectrum against both Gram positive and Gram negative bacteria, in particular against Enterobacteriaceae. (See e.g., U.S. Pat. Nos. 4,284,629, 4,499,091, 4,704,459, 4,668,784, 4,670,444, 5,286,754, and 5,840,333).

Ciprofloxacin is a chemotherapeutic agent. Its use as an antimicrobial agent has distinct advantages over the use of antibiotics (e.g., penicillins, cephalosporins, aminoglycosides, sulphonamides and tetracyclines) in that ciprofloxacin does not induce tolerance or resistance in bacteria. Ciprofloxacin is also known to have low toxicity to humans.

The orally administered quinolone-containing formulations can be prepared by a wet granulation process as described by Y. Shirai et al., *Biol. Pharm. Bull.*, 16(2), 172 (1993). However, the formulations produced by the wet granulation process have a tendency to generate hydrates, thus making the granules less soluble or more difficult to disperse when compared with the corresponding anhydrous form. This results in a delay in the dissolution and a delay in the release of the active ingredient, which may be a nuisance in the use of antimicrobial medicinal products.

Quinolone-containing formulations can also be prepared by a direct compression of the mixture of the quinolone with excipients, without the prior addition of mixing water. See U.S. Pat. No. 5,840,333. However, the direct compression of the mixture of the quinolone ingredient and the excipients in powder form may affect the quality of the tablets due to cleavage problems, which render some batches of tablets unsuitable for marketing.

Recently, Streuff et al. (U.S. Pat. No. 5,286,754) have disclosed an oral formulation of ciprofloxacin which is prepared by combining ciproflaxacin with cellulose as a dry binder, starch, cellulose derivatives and/or cross-linked polyvinylpyrrolidone as a disintegrant, a flow-improving agent such as Aerosil®, a highly pure X-ray-amorphous silicon dioxide, with and NAL® and NAL® RS [a pulverulent product prepared from rice starch]) and a lubricant (such as talc, calcium stearate, magnesium stearate and solid polyethylene glycols).

However, Streuff et al.'s formulation is practically prepared in dry state, although in one variant granulation can be made in a fluidized bed granulator by instantaneously spraying the formulation with water and passing it in warm air, a process which in fact results in simultaneous drying of the granules. Therefore, it is conceivable that the tablets obtained from such preparation may not be satisfactory, possibly due to cleavage problems.

In addition, Streuff et al.'s formulation requires the use of microcrystalline cellulose as the dry binder. Microcrystalline cellulose comes from natural plant fibers through complex micronization. Therefore, the high quantity of microcrystalline cellulose used by Streuff et al. not only drives up the cost of manufacturing the product but also is wasteful and therefore environmentally undesirable. In addition, microcrystalline cellulose is practically insoluble in water. Thus, the use of microcrystalline cellulose in Streuff et al.'s formulation has limited the utility of compounding such formulations in a wet state.

The present invention includes ciprofloxacin-containing formulations produced by a dry-wet-dry granulation process, which is significantly different from either the wet granulation or the dry-mixing processes described above. The process of the present invention begins with mixing the solid dosage form of ciprofloxacin with certain excipients in their dry state, followed by a wet mixing and granulation step wherein a water-solvent solution (e.g., a 1:1 (v/v) water:isopropanol solution) is added to the dry ciprofloxacin-excipients mixture. Finally, the wet granules produced by the wet mixing and granulation step are dried and compressed into solid dosage form of tablets. The present invention is significantly different from that of Streuff et al. because it does not use cellulose as dry binder. The tablets or granules produced from this method have superior bioavailibity and shelf-life than other ciprofloxacin-containing products on the market.

SUMMARY OF THE INVENTION

The present invention provides three kinds of orally administered antimicrobial formulations which contain, as an active ingredient, a solid dosage form of 1-cyclopropyl-6-fluoro-1,4-dihydro-4-oxo-7-(1-piperazinyl)-3-quinolinecarboxylic acid (also called ciprofloxacin) or its pharmacologically acceptable salts. The formulations can be marketed as tablets or capsules. They are non-toxic, highly dispersible, and have excellent storage stability.

The first antimicrobial formulation comprises (1) 60–75 wt % of ciprofloxacin or its pharmacologically acceptable salts; (2) 0.3–10 wt % of pregelatinized starch as binder; (3) 5–30 wt % of lactose as diluent; (4) 1–10 wt % of sodium starch glycolate as disintegrant; and (5) 0.5–2 wt % of magnesium stearate as lubricant. The formulation is prepared by a dry-wet-dry granulation method. The preferable pharmacologically acceptable salt of ciprofloxacin is the monohydrochloride monohydrate salt of ciprofloxacin. The preferable pregelatinized starch is partially pregelatinized starch. A 0.3–3 wt % of sodium lauryl sulfate can be added to the formulation as a wetting agent.

The second antimicrobial formulation comprises (1) 60–75 wt % of ciprofloxacin or its pharmacologically acceptable salts; (2) 1–5 wt % of polyvinyl purrolidone (PVP) as a binder; (3) 5–30 wt % of lactose as a diluent; (4) 1–10 wt % of sodium starch glycolate as a disintegrant; and (5) 0.5–2 wt % of magnesium stearate as a lubricant. The formulation is prepared by a dry-wet-dry granulation method. The preferable pharmacologically acceptable salt of ciprofloxacin is the monohydrochloride monohydrate salt of ciprofloxacin. The preferable PVP is PVP-K30 which has a molecular weight of 40,000. A 0.3–3 wt % of sodium lauryl sulfate can be added to the formulation as wetting agent.

The third antimicrobial formulation comprises (1) 60–75 wt % of ciprofloxacin or its pharmacologically acceptable salt; (2) 1–8 wt % of polyvinyl alcohol (PVA) as a binder; (3) 5–30 wt % of lactose as a diluent; (4) 1–10 wt % of sodium starch glycolate as a disintegrant; and (5) 0.5–2 wt % of magnesium stearate as a lubricant. The formulation is prepared by a dry-wet-dry granulation method. The preferable pharmacologically acceptable salt of ciprofloxacin is the monohydrochloride monohydrate salt of ciprofloxacin. A 0.3–3 wt % of sodium lauryl sulfate can be added to the formulation as wetting agent.

The above three antimicrobial formulations are further compressed into tablets. The tablets are coated by a coating material which comprises hydroxylpropylmethyl-cellulose (HPMC), water, polyethyleneglycol (PEG), dimethylpolysiloxane (DMPS), and $TiO_2$. The preferably weight ratio of HPMC:PEG:DMPS:$TiO_2$ is 73:16.7:0.3:10.

The present invention also provides methods for making the ciprofloxacin-containing granules or tablets. The method of making granules containing the three formulations comprises the steps of: (1) mixing the ciprofloxacin or its pharmacologically acceptable salt with a dry binder (i.e., pregelatinized starch, PVP, or PVA), lactose, and half of the amount of sodium starch glycolate to form a dry powder mixture; (2) mixing the dry powder mixture with a water-solvent solution to form a wet powder mixture; (3) grinding and granulating said wet powder mixture to form wet granules; and (4) drying the wet granules to form dry granules. The dry granules can be either encapsulated or compressed into tablets. The water-solvent solution can be a mixture of water-ethanol, water-isopropanol, and water-acetone. A water-isopropanol solution with 1:1 volume ratio is the preferable one.

The method of making the ciprofloxacin-containing tablets comprises the steps of: (1) mixing ciprofloxacin or its pharmacologically acceptable salt with a dry binder (e.g., pregelatinized starch, PVP, or PVA), lactose, and a half amount of sodium starch glycolate to form a powder mixture; (2) mixing said powder mixture with a water-solvent solution to form a wet powder mixture; (3) grinding and granulating said wet powder mixture to form wet granules; (4) drying the wet granules to form dry granules; (5) mixing the dry granules with the other half amount of sodium starch glycolate, together with magnesium stearate and sodium lauryl sulfate to form a granule mixture; and (6) compressing the granule mixture into said tablet.

DETAILED DESCRIPTION OF THE INVENTION

Figure 1:
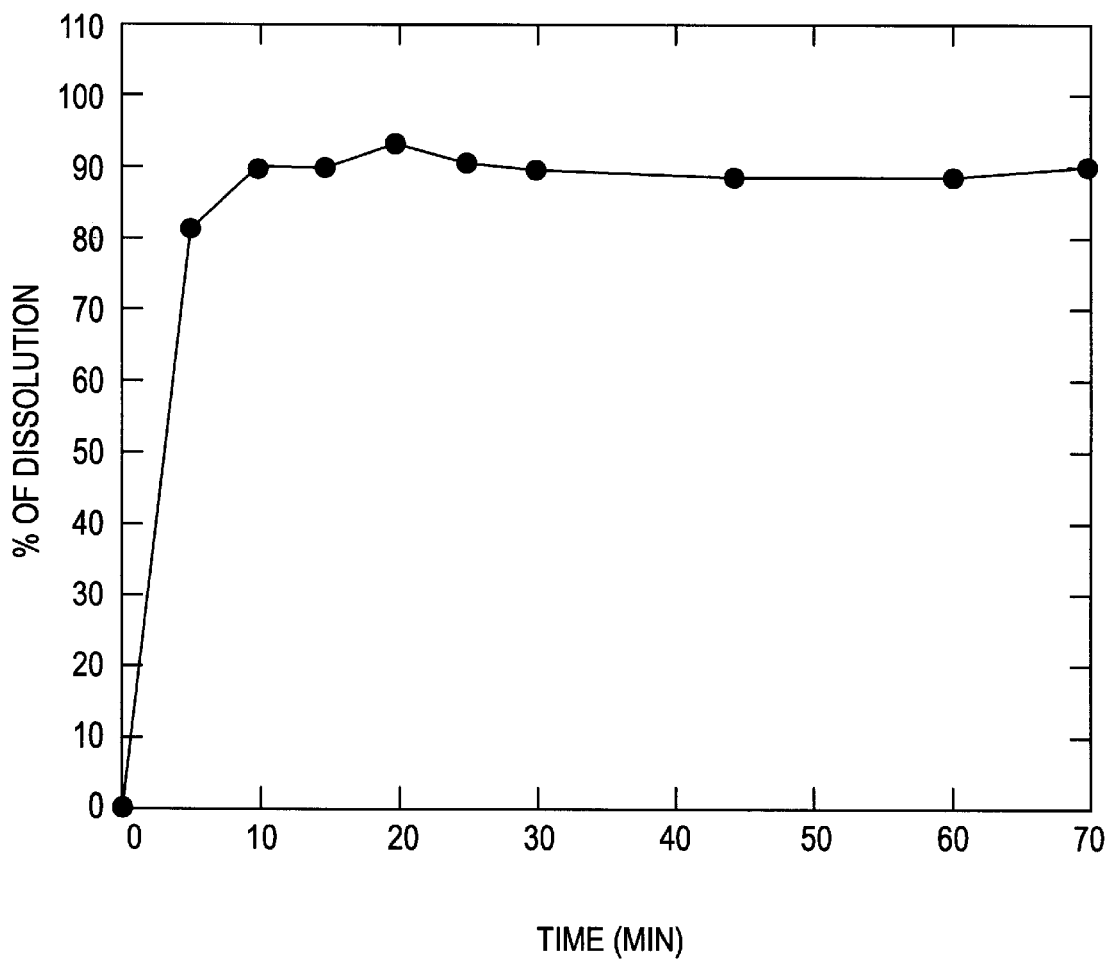
FIG. 1 shows the dissolution rates (%) of tablets containing the formulation of EXAMPLE 1 (infra) at various times. The tablets were coated with a coating material as described in EXAMPLE 7 (infra).

The first embodiment of this invention provides three orally administrable antimicrobial formulations which contain, as an active ingredient, 1-cyclopropyl-6-fluoro-1,4-dihydro-4-oxo-7-(1-piperazinyl)-3-quinolinecarboxylic acid (also called ciprofloxacin) or its pharmacologically acceptable salts in a solid dosage form. These formulations can be sold in the form of granules, granule-containing capsules, powders, sublinguals, or tablets.

The salt forms of ciprofloxacin contain, for example, the inorganic or organic acids (e.g., hydrochloric acid, hydrobromic acid, hydroiodic acid, sulfuric acid, phosphonic acid, acetic acid, succinic acid, malic acid, etc.) of ciprofloxacin, or inorganic or organic bases (e.g., KOH, NaOH, $Ca(OH)_2$, $Al(OH)_3$, piperidine, morpholine, ethylamine, triethylamine etc.) of ciprofloxacin. The preferable salt form of ciprofloxacin is the monohydrochloride monohydrate.

In addition to ciprofloxacin or its pharmaceutically acceptable salts, each of the three formulations contains (1) a binder, (2) a diluent, (3) a disintegrant, and (4) a lubricant. In the first formulation, pregeletinized starch is used as binder. In the second formulation, polyvinyl pyrrolidone (PVP) is used as binder. In the third formulation, polyvinyl alcohol (PVA) is used as binder. The formulations can optionally contain wetting agent. In the case where the formulations are compressed into tablets, a coating material can optionally be coated onto the tablets to improve the dissolution rate of ciprofloxacin.

To mix a binder with the solid dosage form of ciprofloxacin is not only preferable but also necessary, because the solid dosage form of ciprofloxacin has the tendency to break up during granulation and compression. Suitable binders for this purpose should be ones which possess high adhesive effects and which can improve the hardness of the formulations. The three binders, namely, pregelatinized starch, PVP, and PVA, which have been chosen for the ciprofloxacin formulations, share the additional common advantages of inexpensiveness and good water solubility.

There are two kinds of pregelatinized starch: the partially pregelatinized starch and the fully pregelatinized starch. Partially pregelatinized starch is more preferable because it is less expensive, easily available, and has excellent adhesive properties. The partially pregelatinized starch can be handled in the same way as handling starch powder. In fact, once the partially pregelatinized starch has been dispersed in cold water or water-organic solvent, it can display the same viscosity as starch after gelatinization. The use of the partially pregelatinized starch in the formulation can also prevent adhesion of granules to the mold during the compressing process.

Preferably, the amount of pregelatinized starch used as a binder for ciprofloxacin is limited to no more than 13 wt % of the total formulation. If the amount of the partially pregelatinized starch added is too high, it impedes or even halts the disintegration of tablets. Most preferably, the optimal amount of pregelatinized starch used as ciprofloxacin binder is in the range of 0.3 to 10 wt %.

Polyvinyl pyrrolidone (PVP) is another excellent binder. PVP is commonly characterized by the so-called "K-value" as defined by Fikentscher. The K-value of PVP may be calculated by the following equations:

$$\log z = c \frac{75k^2}{1 + 1.5kc} + k \text{ or,}$$

$$K\text{-}value = \frac{\sqrt{300 c \log z + (c + 1.5 \log z)^2} + 1.5 c \log z - c}{0.15 c + 0.003 c^2}$$

where z is the relative viscosity of the solution of concentration c, k is the K-value X $10^{-3}$, and c is the concentration in % (w/v). The K-value of PVP is, therefore, a useful measure of the polymeric composition's viscosity. PVP can be purchased from Tokyo Chemical Industry Co., Ltd. under the trade name of PVP K15, PVP K30, PVP K60, and PVP K90. The preferable PVP to be used as a dry binder for ciprofloxacin is PVP K30, which has an average molecular weight of 40,000. PVP can be used in either wet or dry state. The use of PVP as binder improves the release rate of ciprofloxacin, which in turn increases the uptake rate of ciprofloxacin by humans. The amount of PVP to be used as ciprofloxacin binder should be no more than 10%, and preferably in the range of 0.1–5 wt %.

Polyvinyl alcohol (PVA) is also an excellent binder for solid dosage form compound such as ciprofloxacin. It is non-toxic, water soluble, solvent resistant, and adhesive. The amount of PVA to be used as ciprofloxacin binder should be no more than 10%, preferably in the range of 1–8 wt %.

Diluents which can be used in the ciprofloxacin formulations include lactose, mannitol and sorbitol. The preferable one is lactose due to its low cost, although mannitol and sorbitol may provide a more pleasant taste for the formulations. The optimal amount of lactose used as a diluent is in the range of 5–30 wt %.

A preferable disintegrant used in the ciprofloxacin formulations is sodium starch glycolate, preferably in the range of 2–10%. A lubricant used in the ciprofloxacin formulations can be magnesium stearate, stearic acid, glycerol tribehenate or mixtures of these excipients. A preferable one is magnesium stearate. A preferable wetting agent is sodium lauryl sulfate.

A preferable coating material which can be coated onto the ciprofloxacin tablet comprises, hydroxypropylmethylcellulose (HPMC) as the major component, polyethyleneglycol (PEG), dimethylpolysiloxane (DMPS), and $TiO_2$. A preferable weight ratio of HPMC:PEG:DMPS:$TiO_2$ is 73:16.7:0.3:10.

The present invention also provides a method for making the ciprofloxacin granules or tablets. The present method uses a dry-wet-dry granulation process. First, the solid dosage form of ciprofloxacin or its pharmceutically acceptable salt is homogeneously mixed with a dry binder (such as pregelatinized starch, PVP or PVA), a diluent (such as lactose), and one-half amount of a disintegrant (such as sodium starch glycolate) to form a dry powder mixture. The dry powder mixture is then mixed with water or an aqueous water-organic solvent solution to form a wet powder mixture. The wet powder mixture is further granulated by a high speed granulation machine to form wet granules. At the end of the granulation process, the wet granules are dried and sorted by machine. The dry granules are then mixed with a lubricant (such as magnesium stearate), and the other half amount. of the disintegrant (such as sodium starch glycolate), and optionally, a wetting agent (such as sodium lauryl sulfate) before being compressed into tablets. Optionally, the tablets can be further coated by a coating material which contains hydroxypropylmethylcellulose (HPMC) as the major component, polyethyleneglycol (PEG), dimethylpolysiloxane (DMPS), and $TiO_2$. A preferable weight ratio of HPMC:PEG:DMPS:$TiO_2$ is 73:16.7:0.3:10.

The present dry-wet-dry granulation process has advantages over either wet granulation processes or dry-mixing processes. Advantageously, the initial dry mixing step avoids the generation of hydrates. Similarly, the wet granulation step avoids cleavage problems. Also, the final dry compression step ensures that the tablets can be readily disintegrated or dispersed in aqueous solution once ingested by humans.

The organic solvents which can be used to form the aqueous water-organic solvent solution of the present methods include ethanol, isopropanol, and acetone. These organic solvents can be mixed with water in any combination. A preferable water-solvent solution is a water-isopropanol solution. A preferable ratio of the water-isopropanol solution is a 1:1 ratio (v/v).

The Examples which follow, given without any limitation being implied, illustrate the present invention.

EXAMPLE 1

| | |
|---|---|
| Ciprofloxacin | 65% |
| Pregelatinized starch | 5% |
| Sodium starch glycolate | 5% |
| Lactose | 23% |
| Magnesium stearate | 2% |
| | 100% |

The above formulation was prepared by mixing 416.25 g of ciprofloxacin HCl with 30 g of pregelitinized starch, 15 g of sodium starch glycolate, and 105.75 g of lactose in a high speed mixer to form a powder mixture. Then, 180 ml of water and isopropanol solution (1:1, v/v) was added to the powder mixture to form a wet powder mixture. The wet powder mixture was then loaded onto a high speed granulation machine to be granulated, dried, and sorted. Then, 15 g of sodium starch glycolate, 6 g of sodium lauryl sulfate and 12 g of magnesium stearate were added to the dried granules and mixed until in uniformity. The mixed dried granules were compressed into tablets in a compression machine.

FIG. 1 shows the dissolution rates of the tablet containing the formulation of EXAMPLE 1 between 0 and 70 minutes. The tablets were film-coated by a coating material comprising HHPMC, PEG, DMPS, and $TiO_2$ as described in EXAMPLE 7 (infra). The dissolution rate was measured according to The U.S. Pharmacopoeia (23rd Edition). Briefly, a tablet was put into a container containing 900 ml of pure water. The dissolution test was conducted using a paddle device with the speed set at 50 rpm. The dissolution rate (%) at various times (minutes) was determined based on the amount of ciprofloxacin in the solution compared to the total amount of ciprofloxacin in the tablet. The results shown in FIG. 1 demonstrate that more than 80% of ciprofloxacin was dissociated from the tablet after 5 minutes in water. The dissolution rate of ciprofloxacin plateaued at 90% after 10 minutes of testing.

EXAMPLE 2

| Ciprofloxacin | 70% |
|---|---|
| Pregelatinized starch | 5% |
| Sodium starch glycolate | 5% |
| Lactose | 17% |
| Sodium lauryl sulfate | 1% |
| Magnesium stearate | 2% |
| | 100% |

The above formulation was prepared by the method as described in EXAMPLE 1, except that sodium lauryl sulfate was added to the formulation as wetting agent.

Figure 3:
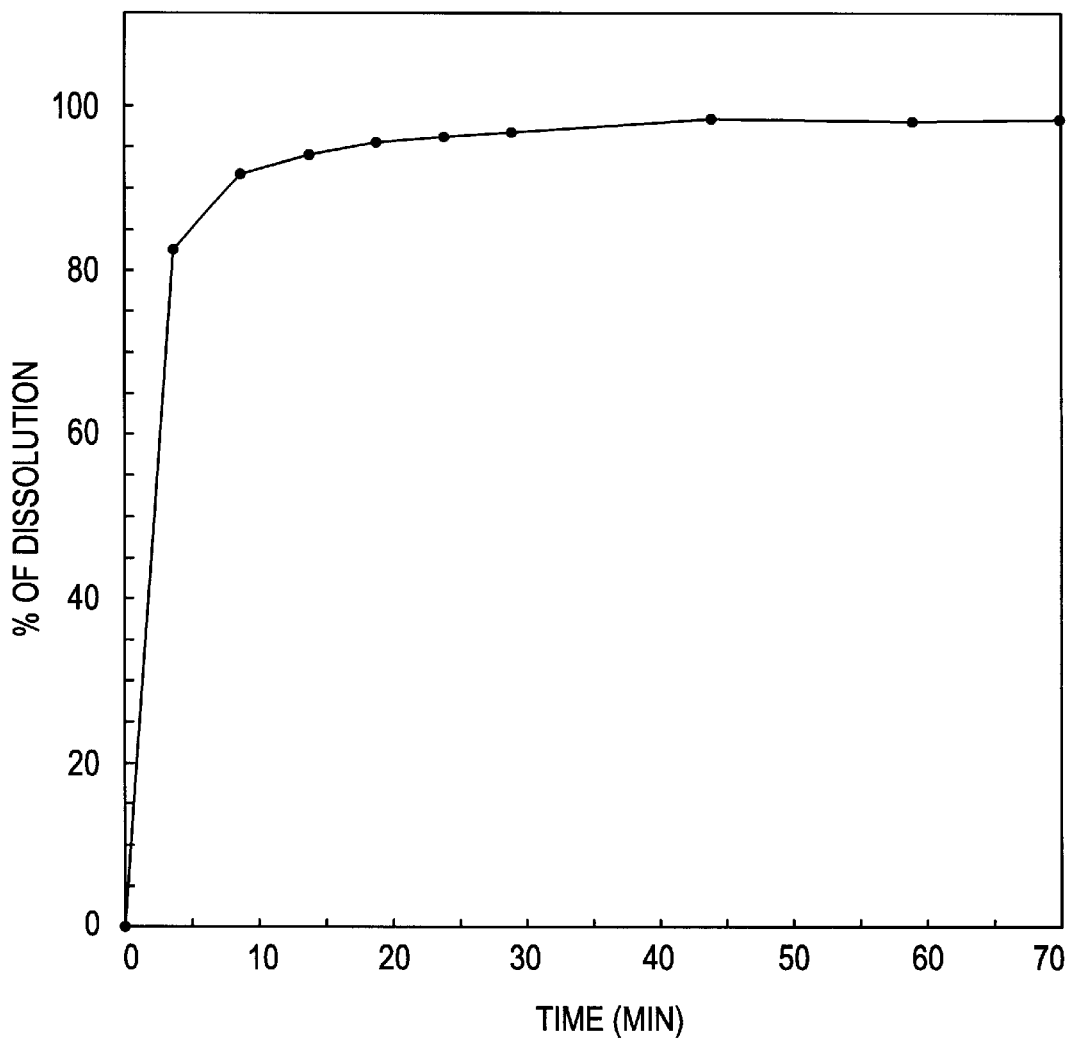
FIG. 3 shows the dissolution rates of tablets containing the formulation of EXAMPLE 2 (infra) at various times. The tablets were coated with a coating material as described in EXAMPLE 7 (infra).

FIG. 3 shows the dissolution rates of tablets containing the formulation of EXAMPLE 2 between 0 and 70 minutes, which were almost identical to that of FIG. 1. The results of FIG. 3 indicate that the addition of sodium lauryl sulfate did not give rise to better dissolution of ciprofloxacin in water.

EXAMPLE 3

| Ciprofloxacin | 70% |
|---|---|
| PVP-K30 | 2% |
| Sodium starch glycolate | 5% |
| Lactose | 21% |
| Magnesium stearate | 2% |
| | 100% |

The above formulation was prepared by the method as described in EXAMPLE 1, except that PVP-K30 was added to replace the pregelatinized starch as binder.

Figure 4:
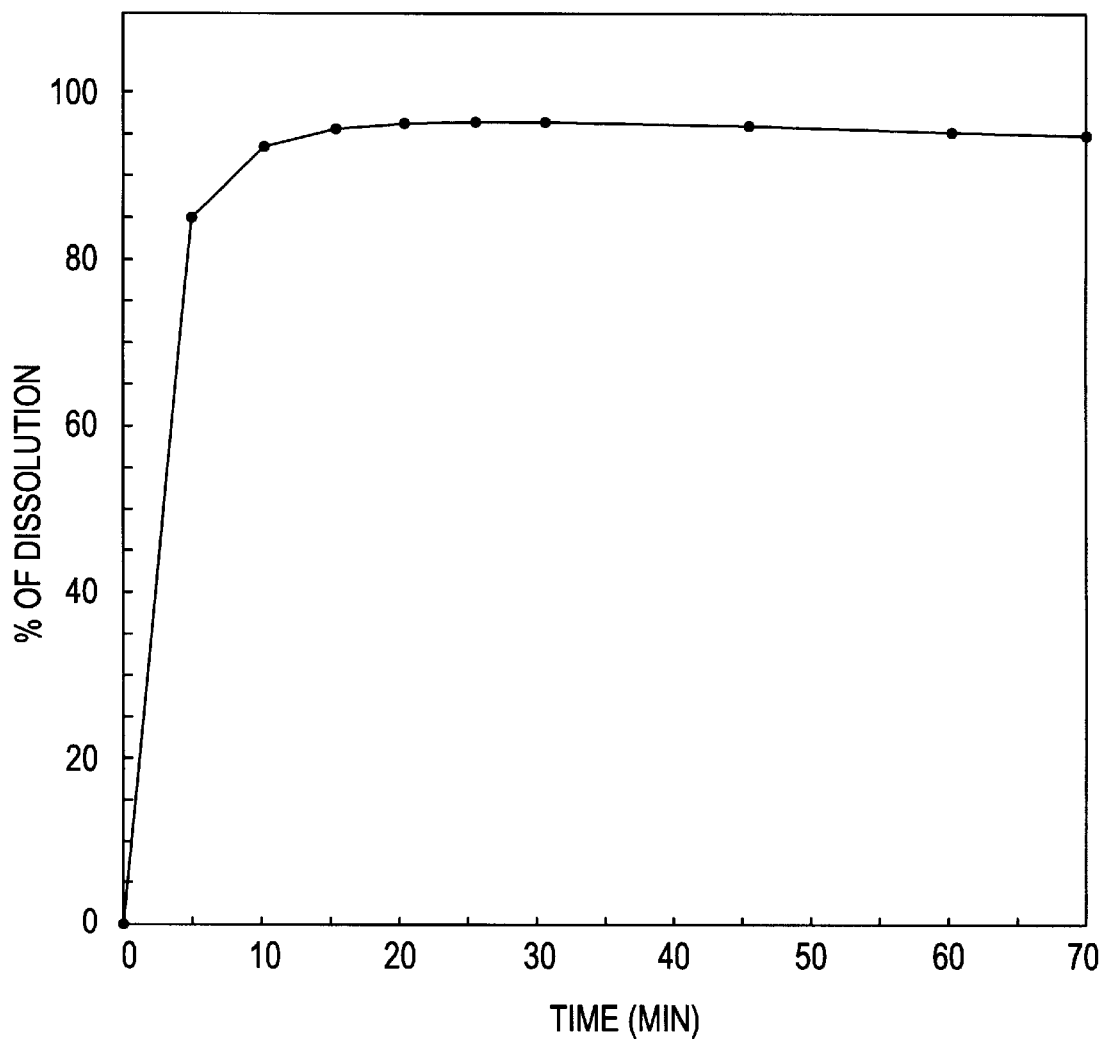
FIG. 4 shows the dissolution rates of tablets containing the formulation of EXAMPLE 3 (infra) at various times. The tablets were coated with a coating material as described in EXAMPLE 7 (infra).

FIG. 4 shows the dissolution rates of the tablet containing the formulation of EXAMPLE 3 between 0 and 70 minutes, which were almost identical to that of FIGS. 1 and 3. The results of FIG. 4 indicate that the replacement of the pregelatinized starch with PVP K30 as binder did not affect the dissolution of the tablet.

EXAMPLE 4

| Ciprofloxacin | 70% |
|---|---|
| PVP-K30 | 2% |
| Sodium starch glycolate | 5% |
| Lactose | 20% |
| Sodium lauryl sulfate | 1% |
| Magnesium stearate | 2% |
| | 100% |

The above formulation was prepared by the method as described in EXAMPLE 1, except that PVP-K30 was added to replace the pregelatinized starch as binder and sodium lauryl sulfate is added as wetting agent.

Figure 2:
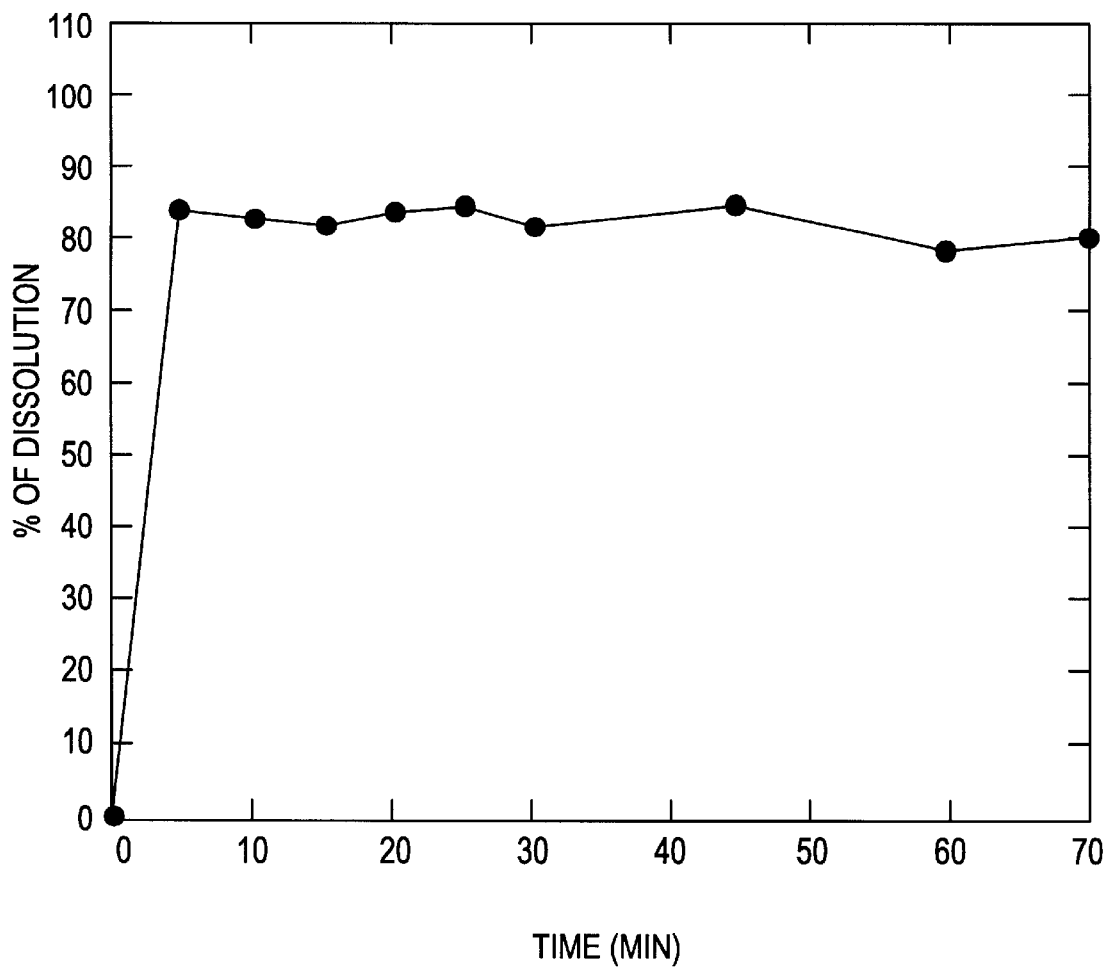
FIG. 2 shows the dissolution rates of tablets containing the formulation of EXAMPLE 4 (infra) at various times. The tablets were coated with a coating material as described in EXAMPLE 7 (infra).

FIG. 2 shows the dissolution rates of the tablet containing the formulation of EXAMPLE 4 between 0 and 70 minutes, which were almost identical to that of FIG. 1 and FIG. 3. The results of FIG. 2 show slightly lower dissolution rates with the maximum dissolution plateaued at 85% after 5 minutes of testing.

EXAMPLE 5

| Ciprofloxacin | 70% |
|---|---|
| Polyvinyl alcohol | 2% |
| Sodium starch glycolate | 5% |
| Lactose | 21% |
| Magnesium stearate | 2% |
| | 100% |

The above formulation was prepared by the method as described in EXAMPLE 1, except that polyvinyl alcohol (PVA) was added to replace the pregelatinized starch as binder.

Figure 5:
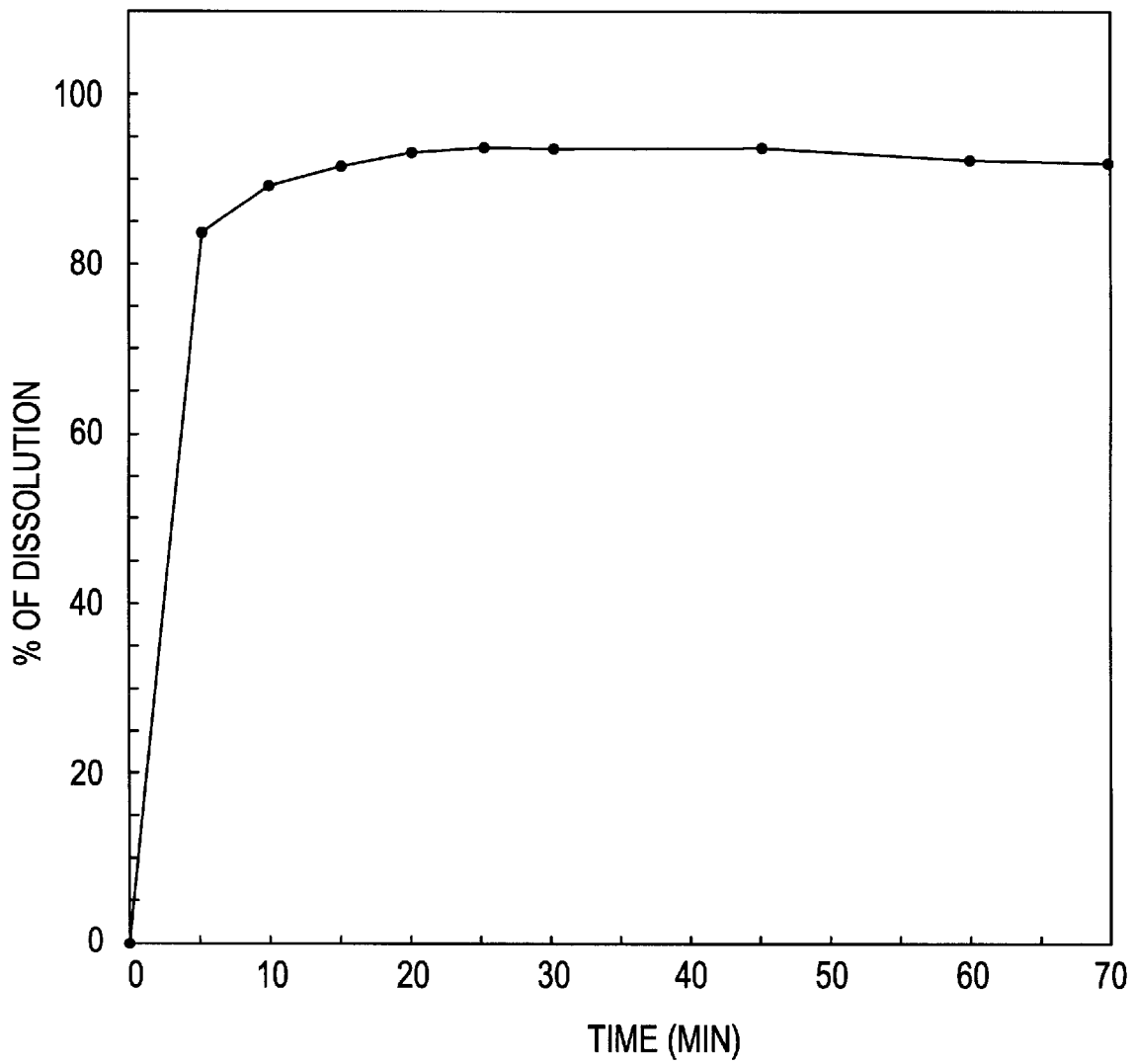
FIG. 5 shows the dissolution rate of tablets containing the formulation of EXAMPLE 5 (infra) at various times. The tablets were coated with a coating material as described in EXAMPLE 7 (infra).

FIG. 5 shows the dissolution rates of tablets containing the formulation of EXAMPLE 5 between 0 and 70 minutes, which were almost identical to that of FIGS. 1, 3–4. The results of FIG. 5 indicate that replacement of the pregelatinized starch or PVP with PVA as binder did not affect the dissolution rate of the tablet.

EXAMPLE 6

| Ciprofloxacin | 70% |
|---|---|
| Polyvinyl alcohol | 2% |
| Sodium starch glycolate | 5% |
| Lactose | 20% |
| Sodium lauryl sulfate | 1% |
| Magnesium stearate | 2% |
| | 100% |

The above formulation was prepared by the method as described in EXAMPLE 1, except that PVA was added to replace the pregelatinized starch or PVP as binder and sodium lauryl sulfate is added as wetting agent.

Figure 6:
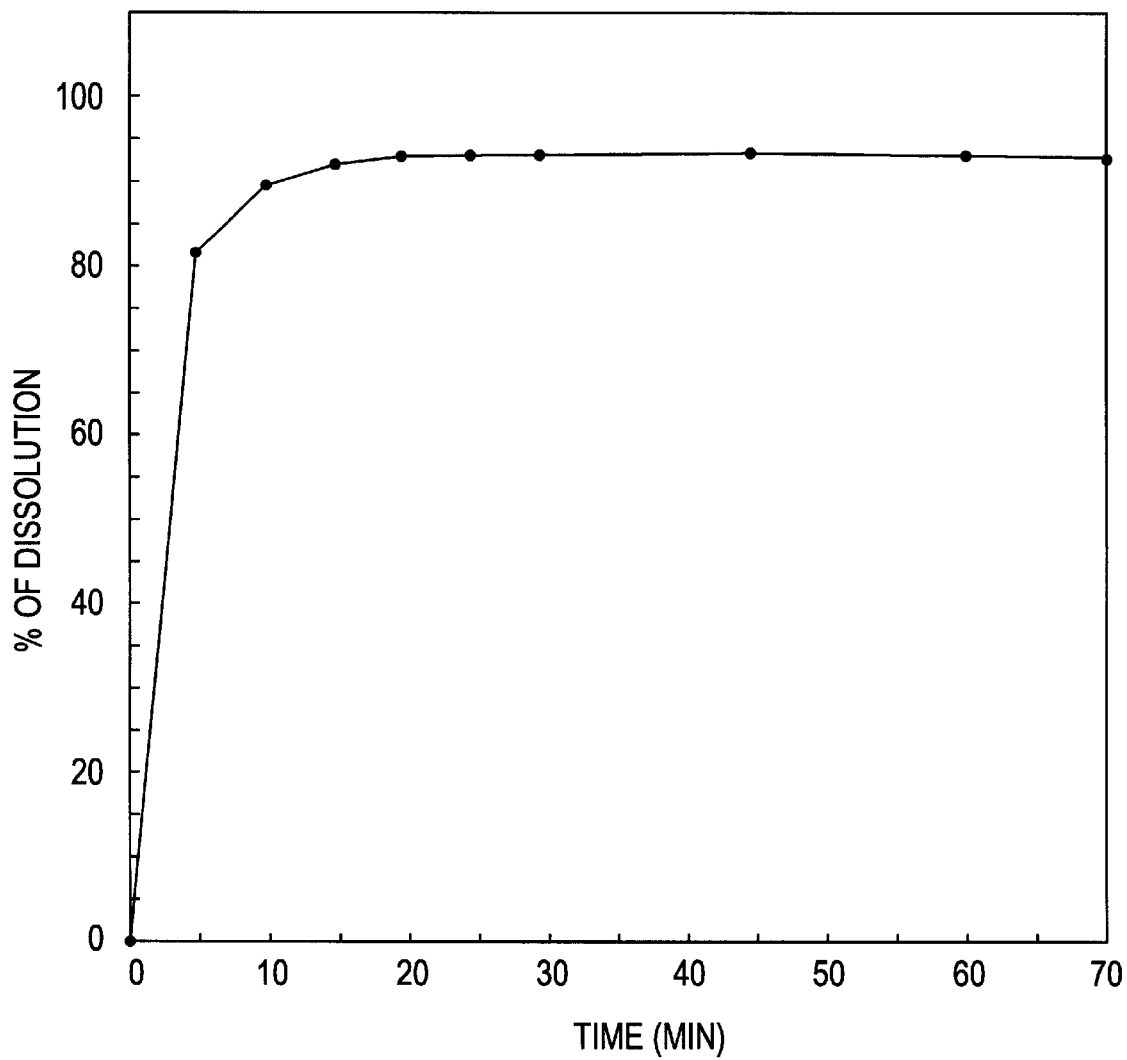
FIG. 6 shows the dissolution rates of tablets containing the formulation of EXAMPLE 6 (infra) at various times. The tablets were coated with a coating material as described in EXAMPLE 7 (infra).

FIG. 6 shows the dissolution rates of tablets containing the formulation of EXAMPLE 6 between 0 and 70 minutes, which were almost identical to that of FIGS. 1, 3–5. The results of FIG. 6 indicate that replacement of the pregelatinized starch or PVP with PVA as binder and the addition of sodium lauryl sulfate did not affect the dissolution rate of the tablet.

EXAMPLE 7

| Hydroxypropylmethyl cellulose (HPMC) | 73% |
|---|---|
| Polyethylene glycol (PEG) | 16.7% |
| Dimethylpolysiloxane | 0.3 |
| $TiO_2$ | 10% |
| | 100% |

EXAMPLE 7 shows the formulation of the coating material. The formulation was prepared by placing 5.475 g of HPMC and 1.2525 g of PEG in a 200 ml beaker in which an adequate amount of hot water was added to facilitate the dispersion of HPMC and PEG. Then, a 0.75 g of $TiO_2$ was added to a 50 ml beaker which was mixed with 20 ml of pure water until uniformity. The $TiO_2$ and water mixture was passed through a 250/in$^2$ sieve once. The sieved $TiO_2$ suspension was then mixed with the HPMC/PEG mixture, of which 0.0225 g of dimethylpolysiloxane was added to bring the final volume to 100 ml with water. The HPMC/PEG/TiO2/DMPS mixture was pass through the 250/in² sieve twice. The sieved HPMC/PEG/TiO2/DMPS mixture, the coating material, was then placed in the spraying gun of the coating machine to spray-coat the surfaces of the tablets as described above.

It should be understood that the foregoing relates only to preferred specific embodiments of the present invention and that numerous modifications or alterations may be made therein without departing from the spirit and the scope of the invention as set forth in the appended claims.

What is claimed is:

1. An orally administered antimicrobial formulation comprising:
   60.0–75.0 wt % of 1-cyclopropyl-6-fluoro-1,4-dihydro-4-oxo-7-(1-piperazinyl)-3-quinolinecarboxylic acid (ciprofloxacin) or at least one of pharmacologically acceptable salt;
   0.3–10.0 wt % of pregelatinized starch as binder;
   5.0–30.0 wt % of lactose as diluent;
   1.0–10.0 wt % of sodium starch glycolate as disintegrant; and 0.5–2.0 wt % of magnesium stearate as lubricant;
   wherein said ciprofloxacin or at least one of pharmacologically acceptable salts, said binder, said diluent, and a half amount of said disintegrant are (A) mixed in a dry state to form a powder mixture, (B) then, mixed with a water-solvent solution to convert said dry powder mixture into a wet powder mixture, (C) then, said wet powder mixture is subject to grinding and granulating to form wet granules, which are further dried to form dry granules; (D) then, said dry granules are mixed with said lubricant and the other half amount of the said disintegrant before compressing into tablets;
   wherein said formulation does not contain cellulose as binder.

2. The orally administered antimicrobial formulation according to claim 1, wherein said pharmacologically acceptable salt of 1-cyclopropyl-6-fluoro-1,4-dihydro-4-oxo-7-(1-piperazinyl)-3-quinolinecarboxylic acid is a monohydrochloride monohydrate salt.

3. The orally administered antimicrobial formulation according to claim 1, wherein said pregelatinized starch is a partially pregelatinized starch.

4. The orally administered antimicrobial formulation according to claim 1, further comprising 0.3–3.0 wt % of sodium lauryl sulfate as wetting agent.

5. A tablet which contains the orally administered antimicrobial formulation according to claim 1, further comprising a coating material, wherein said coating material comprises hydroxylpropylmethylcellulose (HPMC), polyethyleneglycol (PEG), dimethylpolysiloxane (DMPS), and $TiO_2$.

6. The tablet which contains the orally administered antimicrobial formulation according to claim 5, wherein said HPMC, PEG, DMPS and $TiO_2$ is in a weight ratio of 73:16.7:0.3:10.

7. An orally administered antimicrobial formulation comprising:
   60–75 wt % of 1-cyclopropyl-6-fluoro-1,4-dihydro-4-oxo-7-(1-piperazinyl)-3-quinolinecarboxylic acid (ciprofloxacin) or its pharmacologically acceptable salts;
   0.3–10 wt % of pregelatinized starch as binder;
   5–30 wt % of lactose as diluent;
   1–10 wt % of sodium starch glycolate as disintegrant; and
   0.5–2 wt % of magnesium stearate as lubricant;
   wherein said formulation does not contain cellulose as binder.

8. The orally administered antimicrobial formulation according to claim 1, wherein said pharmacologically acceptable salt of 1-cyclopropyl-6-fluoro-1,4-dihydro-4-oxo-7-(1-piperazinyl)-3-quinolinecarboxylic acid is a monohydrochloride monohydrate salt.

9. The orally administered antimicrobial formulation according to claim 1, wherein said pregelatinized starch is a partially pregelatinized starch.

10. The orally administered antimicrobial formulation according to claim 1, wherein said pregelatinized starch is a fully pregelatinized starch.

11. The orally administered antimicrobial formulation according to claim 1, further comprising 0.3–3 wt % of sodium lauryl sulfate as wetting agent.

12. A tablet which contains the orally administered antimicrobial formulation according to claim 1, further comprising a coating material, wherein said coating material comprises hydroxylpropylmethylcellulose (HPMC), polyethylene glycol (PEG), dimethylpolysiloxane (AMPS), and $TiO_2$.

13. A method for making granules containing the orally administered antimicrobial formulation according to claim 1, comprising the steps of:
   mixing a solid dosage form of 1-cyclopropyl-6-fluoro-1,4-dihydro-4-oxo-7-(1-piperazinyl)-3-quinolinecarboxylic acid or at least one of pharmacologically acceptable salt with lactose, pregelatinized starch and a half amount of sodium starch glycolate to form a dry powder mixture;
   mixing said dry powder mixture with a water-solvent solution to form a wet powder mixture;
   grinding and granulating said wet powder mixture to form wet granules; and
   drying said wet granules to form dry granules.

14. The method for making granules according to claim 12, wherein said water-solvent solution is a water-isopropanol solution having a volume ratio of 1:1 (v/v).

15. A method for making a tablet containing the orally administered antimicrobial formulation according to claim 1, comprising the steps of:
   mixing a solid dosage form of 1-cyclopropyl-6-fluoro-1,4-dihydro-4-oxo-7-(1-piperazinyl)-3-quinolinecarboxylic acid or at least one of pharmacologically acceptable salt with lactose, pregelatinized starch and a half amount of sodium starch glycolate to form a powder mixture;
   mixing said powder mixture with a water-solvent solution to form a wet powder mixture;
   grinding and granulating said wet powder mixture to form wet granules;
   drying said wet granules to form dry granules;
   mixing said dry granules with the other half amount of sodium starch glycolate, together with magnesium stearate and sodium lauryl sulfate to form a granule mixture; and compressing said granule mixture into said tablet.

16. The method for making a tablet containing the orally administered antimicrobial formulation according to claim 15, further comprising the step of:
   adding a coating material to said tablet to form a film-coated tablet, wherein said coating material comprises HPMC, PEG, DMPS, and $TiO_2$ in a weight ratio of 73:16.7:0.3:10.

* * * * *